United States Patent [19]

Pohndorf

[11] Patent Number: 4,658,835
[45] Date of Patent: Apr. 21, 1987

[54] NEURAL STIMULATING LEAD WITH FIXATION CANOPY FORMATION

[75] Inventor: Peter J. Pohndorf, Miami Shores, Fla.

[73] Assignee: Cordis Corporation, Miami, Fla.

[21] Appl. No.: 758,743

[22] Filed: Jul. 25, 1985

[51] Int. Cl.⁴ .............................................. A61N 1/04
[52] U.S. Cl. ..................................... 128/785; 128/642
[58] Field of Search ........... 128/419 C, 419 D, 419 P, 128/642, 731, 783, 784, 785, 786

[56] References Cited

U.S. PATENT DOCUMENTS

| | | | |
|---|---|---|---|
| 4,198,963 | 4/1980 | Barkalow et al. | 128/642 |
| 4,285,347 | 8/1981 | Hess | 128/785 |
| 4,374,527 | 2/1983 | Iversen | 128/785 |
| 4,419,819 | 12/1983 | Dickhudt et al. | 128/785 |
| 4,432,377 | 2/1984 | Dickhudt | 128/786 |
| 4,519,403 | 5/1985 | Dickhudt et al. | 128/785 |

Primary Examiner—Edward M. Coven
Attorney, Agent, or Firm—Henry W. Collins; Thomas R. Vigil

[57] ABSTRACT

The neural stimulating lead includes a hollow lead body and an active fixation stabilizing structure. The stabilizing structure comprises two pairs of laterally projecting vanes and an extendable membrane on a dorsal surface of the lead body adapted to be extended to apply pressure against a dorsal surface of a vertebra to force and hold an electrode on the opposite surface of the lead body against the dura of the spinal cord. The membrane forms a canopy which is extended by causing an expandable material to expand against the membrane when actuated by an actuating material inserted into the lead body.

12 Claims, 6 Drawing Figures

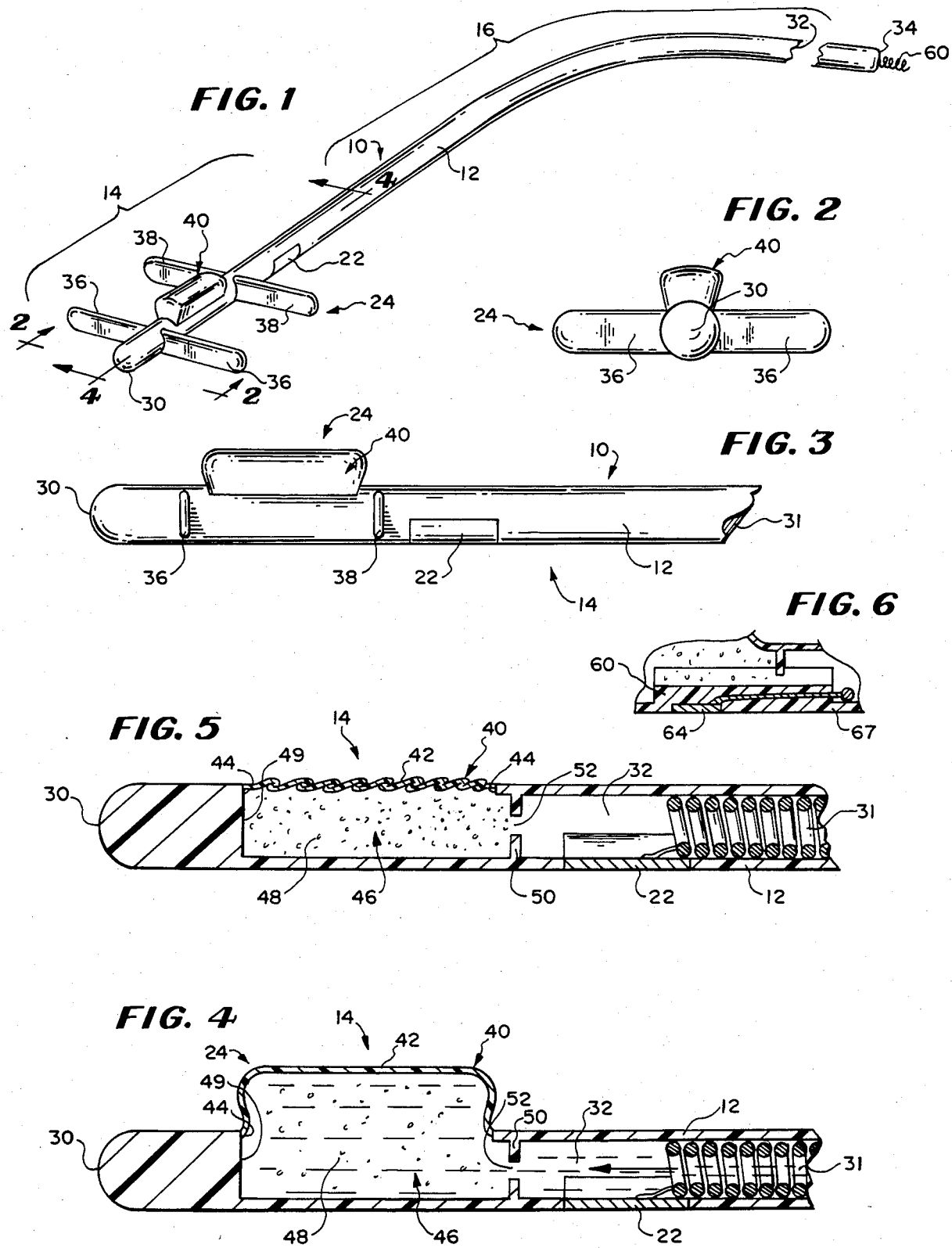

NEURAL STIMULATING LEAD WITH FIXATION CANOPY FORMATION

BACKGROUND OF THE INVENTION

1. Field of the Invention

The present invention relates to a neural stimulating lead including an active fixation stabilizing structure. More specifically, the present invention relates to a stimulating lead having an active fixation stabilizing structure that includes a membrane which can be extended or expanded to form a canopy formation once the stimulating lead has been correctly positioned within an epidural space in a vertebra. The canopy formation serves to fix the position of an electrode on the lead at a desired location along and against the dura of a spinal cord traversing a vertebra of the spine.

2. Description of the Prior Art

Heretofore neural stimulating leads for use in spinal cord stimulation have had a tendency to migrate after placement. The migration has a considerable effect on stimulation, no matter how miniscule the migration is. In this respect, migration of a stimulating lead often results in poor electrical contact of an electrode on the lead with the spinal cord or results in stimulation of an improper are of the spinal cord which will negate the effect required, such as stimulation of a precise area to alleviate pain.

To overcome the problems of such migration, various mechanisms and devices have been proposed. Examples of previously proposed mechanisms and devices are disclosed in the following U.S. patents:

| U.S. PAT. NO. | PATENTEE |
| --- | --- |
| 4,285,347 | Hess |
| 4,374,527 | Iversen |
| 4,419,819 | Dickhudt et al |
| 4,519,403 | Dickhudt |

The Hess U.S. Pat. No. 4,285,347 discloses a neural electrode lead with stabilizing structure. The stabilizing structure here is defined by laterally expandable loop elements.

The Iversen U.S. Pat. No. 4,374,527 discloses a body stimulation lead which includes a plurality of lobes or undulating loops in the lead body for maintaining the position of an electrode at the distal end of the lead. In one embodiment the lobes or loops are in perpendicular planes so as to provide the lead with a crankshaft-like configuration.

The Dickhudt et al. U.S. Pat. No. 4,419,819 discloses a biomedical lead with a lobed lead anchor. The anchor comprises a sleeve which is slit in a direction parallel to the axis of the lead body and when the tubing is compressed, the slit portions expand into lobes to stabilize the position of the lead electrode therein.

The Dickhudt U.S. Pat. No. 4,519,403 discloses a neural stimulating lead having an inflatable balloon which is sealed against a first side of the lead so it inflates away from the first side which is against the dura in an epidural space to urge an electrode on the first side against the dura.

Also, there is proposed in copending application Ser. No. 667,228 a neural stimulating lead with stabilizing structure including an extendible/retractable tine which is movable between a retracted position and an extended position where the tine engages a dorsal wall surface of a vertebra for anchoring the lead within an epidural space in the vertebra.

As will be described in greater detail hereinafter, the neural stimulating lead of the present invention differs from the previously proposed neural stimulating leads by providing an active fixation stabilizing structure including a membrane on one side of the lead which can be extended or expanded by an expandable material which can be actuated to swell/expand against the membrane to form a canopy which bears against a dorsal surface of a vertebra to anchor the lead within an epidural space in a vertebra and force an electrode on the other side of the lead against the dura of the spinal cord.

SUMMARY OF THE INVENTION

According to the invention there is provided a neural stimulating lead comprising a hollow lead body having a distal electrode assembly including a side electrode on one side of said lead body and an active fixation stabilizing structure comprising laterally extending vertebra engaging means, dorsal stabilizing means including a movable membrane on the other side of said lead body, and means for moving said membrane from a retracted position to an extended position where said membrane engages a dorsal wall of a vertebra for fixing said lead within an epidural space in a vertebra of a spine, said moving means including an expandable material and actuating means for causing said expandable material to swell and expand against said membrane. The expandable material is preferably a hydrogel material and the actuating means include a wetting agent for wetting the hydrogel to cause it to swell and expand against the membrane.

Further according to the invention there is provided a method of stabilizing the position of a neural stimulating lead having an active fixation stabilizing structure as defined above, said method including the steps of: feeding said lead through an incision and into an epidural space with the vertebrum engaging means lying in a horizontal plane when a patient is supine and such that said membrane can be extended within the epidural space or foramen; positioning said side electrode in a proper position; and once said side electrode is positioned, supplying said actuating means to said expandable material to cause said membrane to be extended to form a canopy until the canopy bears against a dorsal wall surface of a vertebra within which it is positioned for fixing or stabilizing the engagement of said side electrode with the dura of a spinal cord.

BRIEF DESCRIPTION OF THE DRAWINGS

FIG. 1 is a perspective view of a neural stimulation lead including an active fixation stabilizing structure constructed according to the teachings of the present invention.

FIG. 2 is a front end view of the lead shown in FIG. 1 and shows laterally extending tines and an extended canopy formation of the stabilizing structure of the present invention and is taken along line 2—2 of FIG. 1.

FIG. 3 is a side elevational view of the lead shown in FIG. 1 and shows the extended canopy formation.

FIG. 4 is an axial cross-sectional view of a distal end portion of the lead shown in FIG. 1 with the canopy formation extended and is taken along line 4—4 of FIG. 1.

FIG. 5 is an axial cross-sectional view through the distal end portion of the lead shown in FIG. 1 similar to the view shown in FIG. 4 but with a membrane that forms part of the canopy formaton retracted generally flush with the outer surface of the lead.

FIG. 6 is a fragmentary axial cross-sectional view, similar to the view shown in FIG. 5, of a modified lead body where a side electrode of the lead is situated opposite the membrane.

DESCRIPTION OF THE PREFERRED EMBODIMENT

Referring now to the drawings in greater detail, there is illustrated in FIG. 1 a neural stimulating lead 10. As shown, the lead 10 includes a body 12 having a distal end portion 14 and a remaining proximal portion 16. The distal end portion 14 includes a side electrode 22 and an active fixation stabilizing structure 24 positioned distal of the electrode 22 with the remaining portion of the lead body 12 being referred to and identified as the proximal portion 16.

Typically the electrode 22 is a partial sleeve positioned at a distance of 2 to 10 centimeters from a distal tip 30 of the lead 10.

The lead body 12 is hollow for most of its length and has a coiled conductor 31 extending through a lumen 32 thereof. The coiled conductor 31 exits a proximal end 34 of the lead body 12 and is electrically connected between the electrode 22 and a cathode of an external stimulator (not shown).

The electrode 22 is preferably made of a platinum-iridium material, to which one end of the conductor 31 is welded, while the lead body 12 is made of an elastomeric material, e.g., polyurethane.

As shown in FIG. 1, the active fixation stabilizing structure 24 includes two spaced apart pairs of vanes or tines 36, 38 which extend laterally from the lead body 12 ahead of the partial sleeve electrode 22.

As will be described in further detail below in connection with the description of FIGS. 2-5, the stabilizing structure 24 further includes a dorsal stabilizing structure 40 situated on a dorsal facing surface on one side of the lead body 12 opposite the side of the lead body 12 on which the side electrode 22 is located and in an area between the pairs of vanes 36, 38 to enable the stabilizing structure 24 to provide dorsal/ventral stabilization. The pairs of vanes 36, 38 provide stabilization against lateral movement and the dorsal stabilizing structure 40 provides dorsal stabilization.

As shown in FIG. 2, each laterally projecting pair of vanes 36, 38 comprises two laterally extending vanes 36 or 38 which are in the form of wing-like structures that extend laterally outwardly from each side of the lead body 12 and which are utilized for lateral stabilization of the side (bottom) electrode 22 once the electrode 22 is properly positioned within an epidural space (not shown) of a vertebra.

As best illustrated in FIG. 3, the dorsal stabilizing structure 40 is a canopy type structure which can be referred to as a canopy or canopy formation 40 and which extends upwardly in a dorsal direction from the lead body 12 when the lead body 12 is properly positioned within the epidural space of a vertebra (not shown). As will be defined in greater detail hereinafter, when the canopy 40 is erected on one side of the distal end portion 14, it will force the side electrode 22 on the other side of the distal end portion against the spinal cord, i.e. the dura of the spinal cord, to assure good electrical contact therewith and to provide stabilization of the electrode 22 against dorsal movement away from the spinal cord.

Turning now to FIG. 4, there is illustrated therein an enlarged axial cross-sectional view through the distal end portion 14 of the lead 10 of the present invention. As shown the dorsal stabilizing structure 40 includes a membrane 42 which is extended or expanded to form the canopy formation 40. The membrane 42 is preferably made of a Silastic ™ elastomer or similar material and is secured over an opening 44 in the distal end portion 14 of the lead body 12 which has a hollow compartment 46 beneath the opening 44. The compartment 46 is filled with a specific amount of an expandable material 48, preferably, a hydrogel material 48 such as polyhydroxyalkylmethacrylate (pHEMA) of the type produced by Alcolac Inc. of Baltimore. This hydrogel material 48 is actuated or activated by wetting to cause the material 48 to swell, as shown in FIG. 4, to expand or extend the membrane 42 to form the canopy formation 40.

In this respect, as the hydrogel 48 is wetted, it swells to cause the membrane 42 to stretch and thus form the canopy formation 40 on the dorsal side of the lead body 12 as illustrated in FIG. 4.

The compartment 46 is defined between a front internal wall 49 and a rear internal wall or baffle 50 within the distal end portion 14 of the lead body 12. The baffle 50 has an aperture 52 therein communicating the compartment 46 with the lumen 32 of the lead body 10 at a position just ahead of the side electrode 22. The baffle or wall 50 serves to hold or retain the hydrogel 48 in the compartment 46, while the aperture 52 allows the hydrogel 48 to be easily wetted, such as with water, via the lumen 32.

In use, a stiffening stylet (not shown) is inserted into and through the lumen 32 to assist in controlling movement of the lead 10 during implantation of the electrode 22 of the lead 10. In implantation, the lead body 12 is fed through a TUOHY needle which had been inserted within an appropriate space between vertebrae to a position within an epidural space in a vertebra.

Once the electrode 22 of the lead 10 has been located within an epidural space in an appropriate vertebra, a proximal end 60 of the coiled conductor 31 which exits the proximal end 34 of the lead body 12 is electrically connected to a cathode of an external stimulator, with an anode of the stimulator being connected to a metal instrument in contact with the patient. The TUOHY needle through which the lead body 12 has been fed is a logical choice of metal instrument for such connection.

Then, the stimulator is turned on, and the lead 10 is moved about within the epidural space along the spinal cord until a position along the spinal cord is located where the patient, who is awake during the procedure, indicates a sought after effect, e.g., the absence of pain.

Once this optimum position has been attained, distilled water is injected into the proximal end of the lead body 12 and through the lumen 32 thereof into the compartment 46. As the water flows into the compartment 46, the hydrogel material 48 swells or expands and applies pressure against the membrane 42 to force the membrane 42 to unfold from the position of same shown in FIG. 5, where the membrane 42 had been folded into ruffles so as to be generally flush with the surface of the lead body 10, thereby to move the membrane 42 away from the lead body 12 and against a dorsal wall of the vertebra within which it is located.

The expanded hydrogel 48 serves to wedge the canopy formation 40 outwardly from the lead body 12 and against the dorsal wall of a vertebra to cause the electrode 22, opposite the membrane 42, to bear against the dura of the spinal cord. At the same time, this wedging action serves to fix the stabilizing structure 24 in the epidural space and hold the distal end portion 14 of the lead body 12 in a desired location in the epidural space.

In other words, as the membrane 42 is extended, it wedges against the dorsum of a vertebra within which it is located and the upper surface thereof takes on the shape of the dorsal wall of the vertebra.

In FIGS. 3–5 the electrode 22 is shown positioned opposite and slightly rearwardly of the membrane 42, and to provide more direct pressure of the electrode against the dura, it can be located directly opposite the membrane 42. Such a modified structure is shown in FIG. 6 where a wall portion 60 of a lead body 62 is thicker in the area opposite the membrane for mounting a partial sleeve, side electrode 64.

As described above, the neural stimulating lead 10 with the stabilizing structure 24 of the present invention has a number of advantages, some of which have been described above and others of which are inherent in the invention.

For example, since the dorsal stabilizing structure 40 includes an extendable membrane 42, it has no solid structures which can injure the bone of the vertebra against which it bears.

Also, modifications can be made to the neural stimulating lead 10 having the active fixation stabilizing structure 24 of the present invention without departing from the teachings of the present invention. Accordingly, the scope of the invention is only to be limited as necessitated by the accompanying claims.

I claim:

1. A neural stimulating lead comprising a hollow lead body having a distal electrode assembly including a side electrode on one side of said lead body and an active fixation stabilizing structure comprising laterally extending vertebra engaging means, dorsal stabilizing means including a movable membrane on the side of said lead body oposite said one side, and means for moving said membrane from a retracted position to an extended position where said membrane engages a dorsal wall of a vertebra for fixing said lead within an epidural space of the vertebra of a spine, said moving means comprising an expandable material and actuating means for causing said expandable material to swell and expand against said membrane, said expandable material comprising a hydrogel and said actuating means including a wetting agent for wetting said hydrogel to cause said hydrogel to swell and expand against said membrane to forms a fixation canopy.

2. The lead of claim 1 wherein said laterally extending vertebra engaging means comprise at least one pair of vanes or tines which extend laterally outwardly from the lead body.

3. The lead of claim 2 wherein said vanes are made of elastomeric material.

4. The lead of claim 2 wherein said vanes are made of polyurethane.

5. The lead of claim 2 wherein said laterally extending vertebra engaging means comprise two pairs of vanes which extend laterally outwardly from the lead body opposite each other, said pairs straddling the area of said lead body where said dorsal stabilizing means are located.

6. The lead of claim 5 wherein said laterally extending vertebra engaging means are positioned just ahead of the side electrode.

7. The lead of claim 5 wherein said electrode is sitatated on said one side of said lead body opposite said membrane.

8. The lead of claim 1 wherein said electrode is situated on said one side of said lead body opposite said membrane.

9. The lead of claim 1 wherein said lead body has an opening in the side thereof and said membrane extends over said opening to function as an extendable fixation canopy 10. The lead of claim 9 wherein said membrane is made of an elastomeric material.

11. The lead of claim 9 wherein said membrane, when extended, has an elongate configuration which extends axially of said lead body and radially outwardly from the lead body.

12. A method of stabilizing the position of a neural stimulating lead having an active fixation stabilizing structure as defined in claim 1, said method including the steps of: feeding said lead through an incision and into an epidural space with the vertebra engaging means lying in a horizontal plane when a patient is supine and such that said membrane can be extended within the epidural space or foramen; positioning said side electrode in a position against the dura; and once said side electrode is positioned, supplying said actuating means to said expandable material to cause said membrane to be extended to form a canopy until the canopy bears against a dorsal wall of a vertebra within which it is positioned for fixing or stabilizing the engagement of said side electrode with the dura of a spinal cord.

* * * * *